(12) United States Patent
Vuong (10) Patent No.: US 11,396,500 B2
(45) Date of Patent: *Jul. 26, 2022

(54) HEAT AND OXIDATION RESISTANT Δ⁹ TETRAHYDROCANNOBINOL (THC) AND CANNABINIOL (CBD) COMPOUND AND METHOD OF MANUFACTURING THE SAME

(71) Applicant: Dieu Cam Vuong, Milpitas, CA (US)

(72) Inventor: Dieu Cam Vuong, Milpitas, CA (US)

(73) Assignee: Dieu Cam Vuong, Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/719,901

(22) Filed: Dec. 18, 2019

(65) Prior Publication Data

US 2021/0188797 A1   Jun. 24, 2021

(51) Int. Cl.
| | |
|---|---|
| *C07D 311/80* | (2006.01) |
| *C07C 39/04* | (2006.01) |
| *A61K 47/36* | (2006.01) |
| *A61K 9/00* | (2006.01) |
| *A61K 45/06* | (2006.01) |

(52) U.S. Cl.
CPC .............. *C07D 311/80* (2013.01); *A61K 9/006* (2013.01); *A61K 47/36* (2013.01); *C07C 39/04* (2013.01); *A61K 45/06* (2013.01)

(58) Field of Classification Search
CPC ........ C07D 311/80; A61K 9/006; A61K 47/36; A61K 45/06; C07C 39/04
See application file for complete search history.

(56) References Cited

U.S. PATENT DOCUMENTS

2017/0362195 A1 * 12/2017 Peet ................. C07C 231/12

FOREIGN PATENT DOCUMENTS

WO  WO-2018175992 A1 * 9/2018 ........... A61K 31/352

* cited by examiner

*Primary Examiner* — Jean P Cornet (57) ABSTRACT

A formula and the process of manufacturing of a cannabinoid compound are disclosed which comprise: a cannabidiol element (CBD) having a first predetermine percentage (%) by weight; a Δ⁹ tetrahydrocannabinol (THC) element having a second predetermine percentage (%) by weight (w/w); and saturated fatty acids having a third predetermined percentage (%) of weight (w/w); wherein the saturated fatty acids improve anti-oxidation and heat resistance to the cannabinoid compound.

6 Claims, 4 Drawing Sheets

HEAT AND OXIDATION RESISTANT Δ⁹ TETRAHYDROCANNOBINOL (THC) AND CANNABINIOL (CBD) COMPOUND AND METHOD OF MANUFACTURING THE SAME

FIELD OF THE INVENTION

The present invention relates generally to cannabis formulations. More specifically, the present invention relates to cannabinol (CBN) compositions with antioxidant and heat resistant substances that preserves the ratio of $\Delta^9$ tetrahydrocannabinol (THC) and cannabinol (CBN) in cannabis plants so that the cannabinol (CBN) compositions deliver the entourage effects to patients.

BACKGROUND ART

Cannabidiol (CBD), cannabinol (CBN), and tetrahydrocannabinol (THC) are natural compounds found in cannabis plants. CBN, THC, and CBD, either individually or combined, can cure many illnesses such as seizure, inflammation, pain, psychosis, nausea, migraines, depression, anxiety, insomnia, glaucoma, low appetite. In addition, these cannabinoids can potentially help alleviate insomnia by causing an overall sense of mind and body tranquility and relaxation. THC is the main psychoactive compound that gives the high sensation. High dosage of THC in the cannabis compounds are deemed controlled-substances by the Federal Drug Administration (FDA) because when THC combines with CB1 receptors—similar to anandamide—it creates a high sensation. Currently, the amount of THC allowed by the U.S. FDA is 0.3%. However, THC is responsible for the majority of the pharmacological effects of the Cannabis sativa plants.

Without THC, CBD is not as effective a medicine as compared with the presence of THC. Furthermore, CBD can neutralize the psychotic effect of THC. Mounting evidence suggests that medical substances may be more effective in their whole and natural state. This phenomenon, called the entourage effect, results when the many components such as CBN, CBD, and terpenes within the cannabis plant interact with the human body to produce a stronger influence than any one of those components alone. The entourage effect is a synergistic effect. For that reason, companies have synthesized THC into dronabinol used in Marinol, a drug used to treat chemotherapy-induced insomnia, nausea, as well as anorexia related to weight loss in AIDS patients. Another drug, Sativex, uses the whole cannabis plants and made of 1:1 ratio of CBD to THC. Sativex also includes Cesamet commonly prescribed for Parkinson's patients. Other patients use Sativex in form of Nabiximols which includes both THC and CBD for the treatments of spasticity and multiple scherosis.

Many companies in the pharmaceutical markets have been trying to convert THC into CBN because the U.S. federal law believes that THC as "no currently accepted medical use and high potential for abuse." THC can be converted to CBN by oxidation and high temperatures. In other words, THC degrades into CBN. But this aging or oxidation process of THC into CBN can be 6 to 7 months. CBN can also be produced after cannabis is heated, a process called decarboxylation, which also converts tetrahydrocannabinolic acid (THCA) and cannabidiolic acid (CBDA) found in raw cannabis into cannabinoids THC and CBD. Since CBN is a cannabinoid and reacts with the endocannabinoid system (ECS), it is said to also have other uses. CBN and CBD are acutely different when it comes to their effect on most consumers' appetites. While CBD can act as a mild appetite suppressant, CBN tends to stimulate one's appetite. A few of the common health conditions that both of these Cannabis compounds are said to aid in treating are epilepsy, anxiety, nausea, insomnia, pain, and inflammation. They have also both been proven to have antibacterial and neuroprotective properties as well.

From the above, there is ample evidence that a formula including CBD, THC, and CBN, as well as terpenes are beneficial to human health. When multiple compounds are combined in their natural state, it does not end up with the sum of each part; instead, a multiplying effect results. The different compounds can amplify each other's chemistry, making the overall plant more effective in addressing unwanted symptoms. The entourage effect becomes especially evident when comparing the effects of tetrahydrocannabinol (THC) (the psychoactive component of the cannabis plant) with the effects of using the whole plant. When pure, synthetic THC became available (as the drug Marinol) in the mid-1980s, scientists expected it to work just as well as using the entire cannabis plant. However, they quickly discovered that patients preferred to use the whole plant instead of Marinol. As it turns out, cannabis contains more active compounds than just THC. Over 85 cannabinoids have been found to work in conjunction with THC to produce the relief that is often reported by cannabis users. In particular, the compound known as cannabidiol (CBD) modulates the effect of THC on the human body. Specially bred cannabis that contains roughly equal amounts of THC and CBD were shown to be the most effective in terms of symptom relief and pain. These findings indicate that the ratio of THC to CBD plays a crucial role in determining the efficacy of the cannabis plant for therapeutic applications.

Not only is the composition of cannabinoid drugs important, the manners they are consumed by the patients are also medically crucial. There are different methods of ingesting cannabinoid drugs: inhalation, oral, sublingual, and topical. Inhalation involves smoking and vaporization that admit the cannabinoids directly into the patient's blood stream through the lungs. However, inhalation is limited by the hazard to the pulmonary function from carbon dioxide ($CO_2$) and carbon monoxide (CO) generated from the burning of other ingredients beside the cannabinoids. Furthermore, inhalation by smoking can convert THC into CBN due to the heat generated from the combustion in the presence of oxygen during the smoking process.

Cannabinoids can also be ingested orally, which can be in the form of edibles, tinctures, capsules, or oils. However, cannabinoids can be destroyed by the stomach acids. Cannabinoids can also enter the blood stream when placed under the tongue and held in the mouth. Within the mouth there are a large number of blood vessels which can absorb cannabinoids. Common examples of these type of products include dissolvable strips, sublingual sprays, or medicated lozenges or tinctures. Sativex, the one clinically approved, cannabinoid medication that includes the entire spectrum of natural cannabinoids, is delivered as a sublingual spray. The time of onset for this method of consumption is similar to those seen in general oral consumption, however, some studies have reported an earlier onset.

Δ9-Tetrahydrocannabinol (THC) is the primary active ingredient of Cannabis sativa (marijuana) and is responsible for the majority of the pharmacological effects of the plant. People have utilized the plant since ancient times for medicinal purposes as well as for its intoxicating properties. To date, the most promising clinical applications approved by the Food and Drug Administration (FDA) are for the control of nausea and vomiting associated with chemotherapy and for appetite stimulation of AIDS patients suffering from anorexia as a result of wasting syndrome. Δ9-Tetrahydrocannabinol (THC), however, demonstrates other biological activities, which lend themselves to possible additional therapeutic applications. These include glaucoma, migraine headaches, spasticity, and anxiety. Also, more recently, THC is becoming recognized as an analgesic. Due to these promising biological activities of THC, marijuana has been advocated for its medicinal value.

Finally, another parenteral method to admit cannabinoids is through topical applications which include lotions, salves, bath salts and oils that are applied to the skin. The skin has a relatively complex absorption process that is based on a chemical's ability to dissolve in $H_2O$. However, this method only works well in localized area such as arthritis. Additionally, the topical application of cannabinoids does not allow a significant amount of cannabinoids to reach the brain and therefore is unlikely to cause any intoxication.

Therefore, what is needed is a cannabinoid medication that can maintain the CBD, THC, CBN, and terpenes ratio and/or percentage of weight in order to be suitable to different patients without any side effects such as psychosis.

Furthermore, what is needed is a cannabinoid medication that can maintain the quality of the CBD, THC, CBN, and terpenes and their relative ratio and/or percentage of weight in order to achieve the entourage effect.

What is needed is a cannabinoid medication that is characterized by oxidation resistance and heat resistance so as to prevent THC from converting into CBN and/or other degradants.

What is needed is a cannabinoid medication that can be delivered sublingually and easy to be absorbed by the patient's body.

The cannabinoid medication of the present invention achieves the above needs and provide solutions to existing problems that are felt by other pharmaceutical manufacturers but fail to solve them.

SUMMARY OF THE INVENTION

Accordingly, an object of the present invention is to provide formula and the process of manufacturing of a cannabinoid medication which comprises: a cannabidiol element (CBD) having a first predetermine percentage (%) by weight; a $\Delta^9$ tetrahydrocannabinol (THC) element having a second predetermine percentage (%) by weight (w/w); and saturated fatty acids having a third predetermined percentage (%) of weight (w/w); wherein the saturated fatty acids are operative to maintain an entourage effect of the cannabidiol element (CBD) and the $\Delta^9$ tetrahydrocannabinol (THC) element.

Another object of the present invention is to provide a process of producing a cannabinoid medication capable of delivering an entourage effect, comprising: (a) providing a cannabis compound having a cannabidiol element (CBD) having a first predetermine percentage (%) by weight, a $\Delta^9$ tetrahydrocannabinol (THC) element having a second predetermine percentage (%) by weight (w/w), a third predetermined percentage by weight, and said fourth predetermined percentage by weight; (b) vacuum drying the cannabis compound in step (a); and mixing the vacuum dried cannabis compound from step (b) with an anti-oxidation and heat resistant compound having a third predetermined percentage (%) by weight (w/w).

Another object of the present invention is to provide a cannabinoid medication that can maintain the CBD, THC, CBN, and terpenes predetermined ratio and/or percentage of weight in order to deliver a suitable dosage to different patients without any unwanted effects.

Furthermore, another object of the present invention is to provide a cannabinoid medication that can maintain the purity and freshness of the CBD, THC, CBN, and terpenes and their relative ratio and/or percentage of weight in order to deliver the entourage effect to the patients.

Yet another object of the present invention is to provide a cannabinoid medication that is characterized by oxidation resistance and heat resistance so as to prevent THC from converting into CBN and/or other degradants.

Yet another object of the present invention is to provide a cannabinoid medication that can be delivered sublingually and easy to be absorbed by the patient's body without any side effects and degradations of the medication.

BRIEF DESCRIPTION OF THE DRAWINGS

The accompanying drawings, which are incorporated in and form a part of this specification, illustrate embodiments of the invention and, together with the description, serve to explain the principles of the invention.

and

DETAILED DESCRIPTION OF THE INVENTION

Reference will now be made in detail to the preferred embodiments of the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of the present invention, numerous specific details are set forth in order to provide a thorough understanding of the present invention. However, it will be obvious to one of ordinary skill in the art that the present invention may be practiced without these specific details. In other instances, well-known methods, procedures, and components have not been described in detail so as not to unnecessarily obscure aspects of the present invention.

Exemplary embodiments and aspects of the present invention are now described with reference to FIG. 1 to FIG. 3. The present disclosure discloses the following features of the present invention: (1) a cannabinoid compounds that can maintain the CBD, THC, CBN, and terpenes ratio and/or percentage of weight in order to deliver a suitable dosage to different patients without any unwanted effects, (2) a cannabinoid compounds that can maintain the quality and freshness of the CBD, THC, CBN, and terpenes and their relative ratio and/or percentage of weight in order to achieve the well-known entourage effect, (3) cannabinoid compounds characterized by oxidation resistance and heat resistance so as to prevent THC from converting into CBN and/or other degradants, and (4) a cannabinoid compounds that can be delivered sublingually and easy to be absorbed by the patient's body without any side effects and degradations of the medication.

Figure 1:
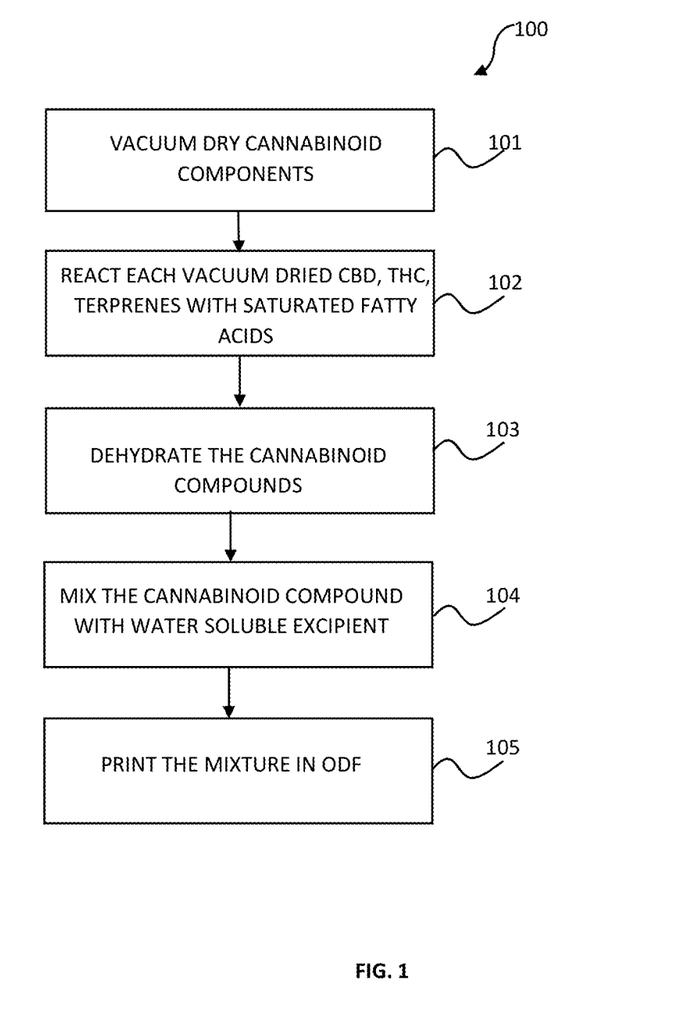
FIG. 1 illustrates a method of producing a cannabinoid compound characterized by heat resistance, oxidation resistance so as to deliver the entourage effects to the patients in accordance with an exemplary embodiment of the present invention.

Now referring to FIG. 1, FIG. 1 is a flow chart illustrating a method 100 method of producing a cannabinoid formula characterized by heat resistant, oxidation resistance to deliver the entourage effects to the patients in accordance with an exemplary embodiment of the present invention. In a generalized structure of the present invention, method 100 includes 3 major components: (a) vacuum drying a cannabis compound having a predetermined ratio of cannabinoid; (b) mixing the vacuum dried cannabinoids with a saturated fatty acid; (c) removing water from the mixture; (d) coating the new cannabinoid compound with a water soluble excipient; and (e) printing the resulted cannabinoid compounds in form of orally disintegrating films (ODF).

At step 101, cannabinoids including, but not limited to, a cannabidiol element (CBD) having a first predetermine percentage (%) by weight, and a $\Delta^9$ tetrahydrocannabinol (THC) element having a second predetermine percentage (%) by weight (w/w) are vacuum dried. In many embodiments of the present invention, cannabinoids to be vacuum dried also includes terpenoids and cannabinol (CBN). Since terpenes, THC, CBN, and CBD have high freezing points at 15° C. Vacuum drying conditions were set at 0.61 Kpa and 15° C. which remove oxygen, thus eliminating product oxidation while lowering the boiling point temperature to lessen heat exposure, Additionally, vacuum drying—under the right conditions—preserves the quality and microstructure of each cannabinoid component.

At step 102, the vacuum dried cannabinoids are mixed with an antioxidant and heat resistant substance such as saturated fatty acids. Since cannabinoids such as CBD, THC, and CBN are soluble in fatty acids and insoluble in water, step 102 is realized by allowing the vacuum dried cannabinoids react with saturated fatty acids ($CH_3(CH_2)_nCOOH$) that are antioxidant and heat resistant in their characteristics at room temperatures and higher. In various implementations of step 102 of the present invention, the antioxidant and heat resistant substance used is stearic acid $CH_3(CH_2)_{16}COOH$. That is, the vacuum dried cannabinoids are mixed with long-chain single carbon bonds of the fatty stearic acid to increase their stability, pharmacokinetic profile, and constant dosage. As a non-limiting example, the following reaction is obtained from step 102:

$$C_{21}H_{30}O_2 + CH_3(CH_2)_{16}COOH \rightarrow C_{41}H_{65}O_2 + H_2O \quad (1);$$

Where $C_{41}H_{65}O_2$ of the present invention has the chemical structure as follows:

Where $R=(CH_2)_nCH_3$ and in this case n=18 which is stearic acid.

Similarly, CBD is reacted with liquid saturated fatty acids such as stearic acid (n=18), the following reaction is obtained:

$$C_{21}H_{30}O_2 + 2(CH_2)_{18}CH_3COOH \rightarrow C_{61}H_{106}O_2 + 2H_2O \quad (2);$$

In this reaction (2), $C_{61}H_{106}O_2$ of the present invention has the following structure:

At step 103, cannabinoid compounds 203 ($C_{41}H_{65}O_2$) and 213 ($C_{61}H_{106}O_2$) are dehydrated to remove water ($H_2O$) from the above reactions. In various embodiments, step 102 and step 103 are performed simultaneously using the heating magnetic stirrer ARE by Velp Scientifica. Since saturated fatty acids are solid at room temperature, the magnetic stirrer ARE is used to heat the fatty acids to 70° C. to liquefy them. Once the saturated fatty acids becomes a liquid, the vacuum dried cannabinoid powders are slowly added to the stirrer. The temperature of the magnetic stirrer continues to increase until the cannabinoids 203 and 213 are formed and all the excess water is removed.

Now at step 104, the cannabinoid compounds 203 and 213 are mixed with oil insoluble and water soluble excipient polymer such as hydroxyl propyl methyl cellulose (HPMC), cellulose derivative gelatin, and/or pullulan. That is, the cannabinoid compounds 203 and 213 are coated with the cellulose which is soluble in water but immiscible with the cannabinoid compounds 203 and 213.

At step 105, the liquid mixture from step 104 is dried up and formed oral disintegrating films (ODF) by casting, printing, or the likes. In many aspects of the present invention, coordinated matrix printing is used to print the mixture in step 104 in ODF. Coordinated matrix printing is a novel method of printing the mixture in step 104 in ODF where errors can be readily fixed without discarding any of the defective ODF strips. Step 105 can be implemented using the novel self-correcting 3D or 4D printing technology described fully in another patent application entitled, "Method and System for Manufacturing of Pharmaceutical Formulas in Form of Orally Disintegrating Film (ODF) by the same inventor, Brandon Vuong, filed as a continuation-in-part application to the present application. In other embodiments of the present invention, the shape and number of ODF units can be predetermined. For example, instead of rectangular ODF units, the cannabinoid mixture of step 104 can be produced in 3D pill shape, oval shape, cylindrical shape, animal shapes, leaf shapes, or any shapes that the market prefers. For example, children prefers animal shape OBD units. In addition, the thickness, and dimension, and the array size of ODB units can be precisely controlled.

Figure 2:
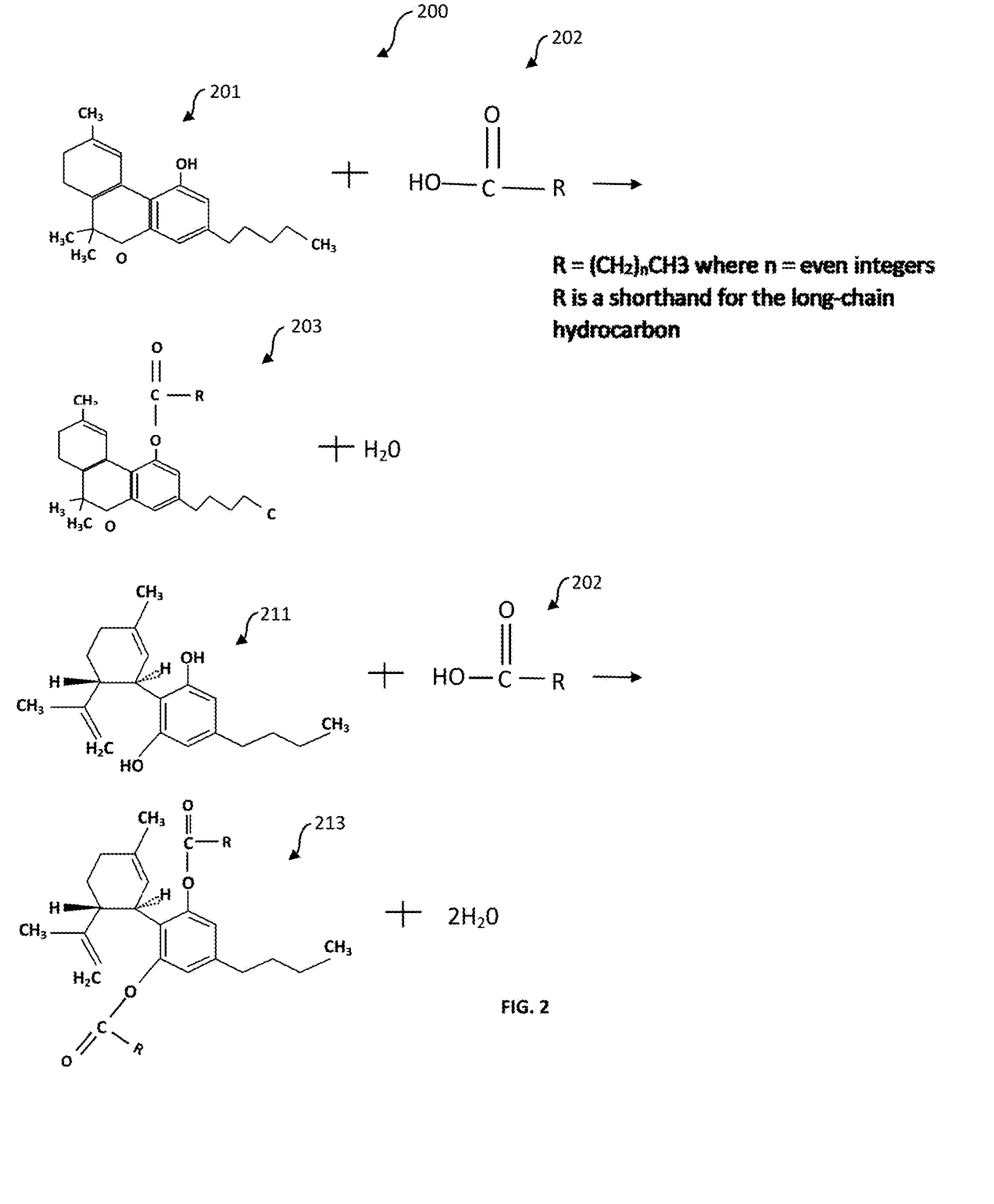
FIG. 2 shows chemical reactions that produce the cannabinoid compounds, i.e., $C_{41}H_{65}O_2$ and $C_{61}H_{106}O_2$ obtained from the process of FIG. 1 in accordance with an exemplary embodiment of the present invention.

Now referring to FIG. 2, chemical reactions to produce the cannabinoid compounds 203 and 213 obtained from method 100 of FIG. 1 are illustrated. Chemical reaction 200 includes a tetrahydrocannabinol (THC) 201, a saturated fatty acid 202 ($CH_3(CH_2)_nCOOH$) such as stearic acid ($CH_3(CH_2)_{16}COOH$) with single bond hydrocarbon chain R. Stearic acid 202 is a saturated monobasic acid with 18 carbon-chain lengths. It is synthesized by the hydrolysis of animal fat or from hydrogenation of cottonseed or vegetable oil. It is noted that similar chemical reactions can be performed for other cannabinoid elements such as CBN and terpenes. Cannabinoid compound 203 is obtained by heating up the stearic acid in a flask of a magnetic stirrer until it is liquefied at about 70° C. Then, the vacuum dried cannabinoid power such as THC 201 is slowly added to the flask and stirred until stearic acid 202 and THC 201 are condensed into new cannabinoid compound 203. Since new cannabinoid compound 203 is immiscible in water, it is separated from water by heating up the compound in a drying process to evaporate all the excess water. The novel cannabinoid compound 203 ($C_{41}H_{65}O_2$) and 213 ($C_{61}H_{106}O_2$) of the present invention achieve the following objectives:

(a) oxidative resistances;

(b) high boiling temperatures due to the long chain of hydro carbon;

(c) purity and microstructures are preserved

Figure 3:
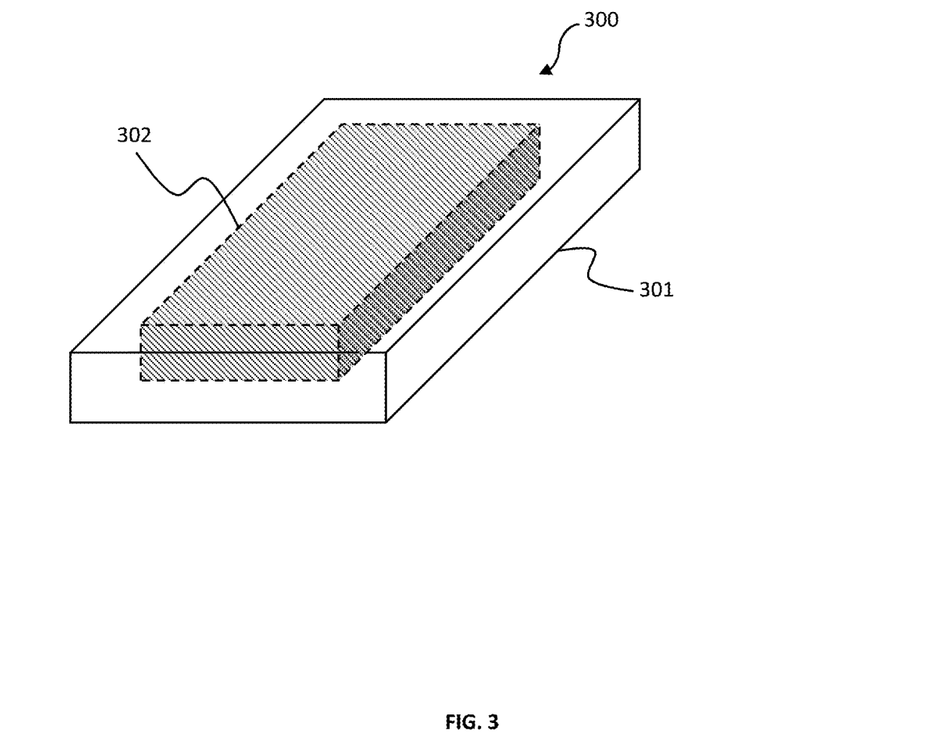
FIG. 3 illustrates a cannabinoid formula that includes cannabinoid compounds as described in FIG. 1 and FIG. 2 and a coating layer in accordance with an exemplary embodiment of the present invention.

Now referring to FIG. 3 which illustrates a cannabinoid formula of the present invention which includes cannabinoid compound 203 or 213 coated by a protective layer in accordance with an exemplary embodiment of the present invention. A cannabinoid formula 300 includes a cannabinoid compound 302 coated by an edible-water-dissolvable polymer 301 ("coating layer 301"). In many embodiments of the present invention, cannabinoid compound 302 is either compound 203 ($C_{41}H_{65}O_2$), compound 213 ($C_{61}H_{106}O_2$). In other embodiments, cannabinoid compound 302 also includes terpenes, CBN reacted with saturated fatty acids as described above in method 100. Coating layer 301 includes hydroxyl propyl methyl cellulose (HPMC), polyglycerol polyricinoleate (PGPR), cellulose derivative gelatin, and/or pullulan. Coating layer 301 is a water dissolvable and bioavailable protective layer that prevent deteriorating agent from degrading cannabinoid compound 302.

Figure 4A:
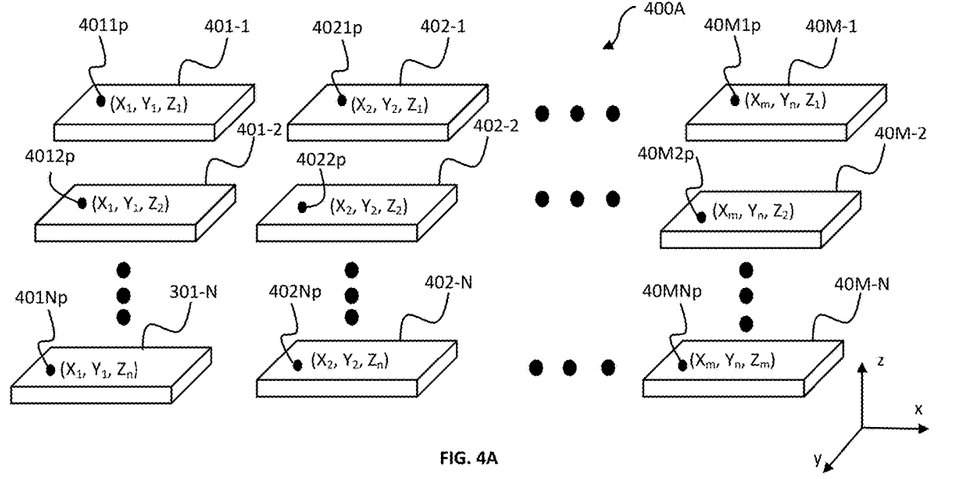
FIG. 4A-FIG. 4B show a perspective three-dimension (3D) of the cannabinoid formula in form of oral disintegrating film (ODF) as an optimal mode of ingestion in accordance with an exemplary embodiment of the present invention.
Figure 4B:
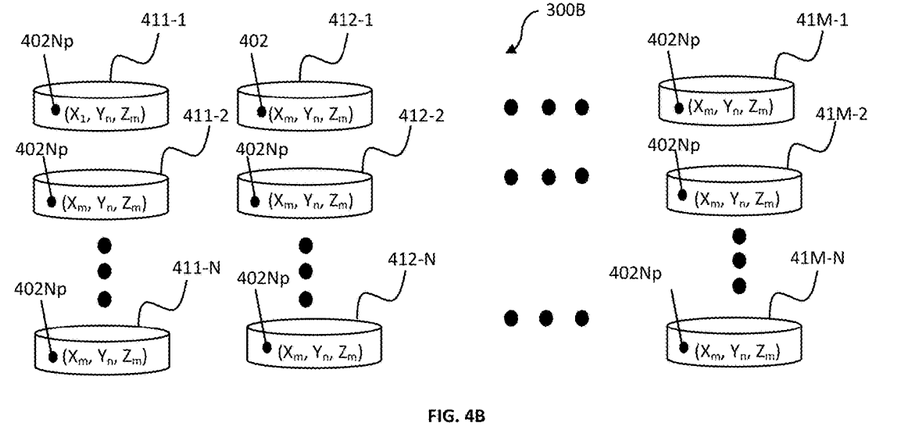

Finally referring to FIG. 4A and FIG. 4B which show a perspective three-dimension (3D) of the cannabinoid formula in form of oral disintegrating film (ODF) as an optimal mode of ingestion in accordance with an exemplary embodiment of the present invention are presented.

Referring to FIG. 4A, an N×M matrix 400A of ODF units in form of 3D rectangular shape is illustrated. Matrix 400A has N rows and M columns, where M and N are non-zero positive integers. Each ODF unit contains has a matrix address of row and column. Matrix 400A contains: in the first row, from left to right: a ODF unit 401-1, 402-1 . . . , and 40M-1; in the second row, from left to right: a ODF unit 401-2, 402-2, . . . , and 40M-2; and in the Nth row (bottom row), from left to right: a ODF unit 401-N, 402-N, . . . , and 40M-N. In the first row, ODF unit 401-1 is constituted by droplets 4011$p$ each having xyz coordinates (xi, yi, zi). Similarly, ODF unit 402-1 has droplets 4021$p$ each having xyz coordinates (xi, yi, zi), ODF unit 40M-1 has droplets 40M1$p$ each having xyz coordinates (xi, yi, zi). In the second row, ODF unit 401-2 is constituted by droplets 4012$p$ each having xyz coordinates (xi, yi, zi). Similarly, ODF unit 402-2 has droplets 4022$p$ each having xyz coordinates (xi, yi, zi), ODF unit 40M-2 has droplets 30M2$p$ each having xyz coordinates (xi, yi, zi). In the last row, ODF unit 401-N is constituted by droplets 401N$p$ each having xyz coordinates (xi, yi, zi). Similarly, ODF unit 402-N has droplets 402N$p$ each having xyz coordinates (xi, yi, zi), ODF unit 40M-N has droplets 40MN$p$ each having xyz coordinates (xi, yi, zi). That way, any ODF units at any particular matrix location can be reprinted and corrected without having to discard any of the defective ones. It is noted that each unit in matrix 400A described above includes cannabinoid medication 300. In different embodiments, each unit 401-1 . . . 40M-N, also includes peppermint oil and other flavonoids.

Now referring to FIG. 4B, an N×M matrix 400B of ODF units in form of 3D oval shape is illustrated. Matrix 400B has N rows and M columns, where M and N are non-zero positive integers. Each ODF unit has a matrix address of row and column. Matrix 400B contains: in the first row, from left to right: a ODF unit 411-1, 412-1, . . . , and 41M-1; in the second row, from left to right: a ODF unit 411-2, 412-2, . . . , and 41M-2; and in the Nth row (bottom row), from left to right: a ODF unit 411-N, 412-N, . . . , and 41M-N. In the first row, ODF unit 411-1 is constituted by droplets 4111$p$ each having xyz coordinates (xi, yi, zi). Similarly, ODF unit 412-1 has droplets 4121$p$ each having xyz coordinates (xi, yi, zi), ODF unit 41M-1 has droplets 41M1$p$ each having xyz coordinates (xi, yi, zi). In the second row, ODF unit 411-2 is constituted by droplets 4112$p$ each having xyz coordinates (xi, yi, zi). Similarly, ODF unit 412-2 has droplets 4122$p$ each having xyz coordinates (xi, yi, zi), ODF unit 41M-2 has droplets 41M2$p$ each having xyz coordinates (xi, yi, zi). In the last row, ODF unit 411-N is constituted by droplets 411N$p$ each having xyz coordinates (xi, yi, zi). Similarly, ODF unit 412-N has droplets 412N$p$ each having xyz coordinates (xi, yi, zi), ODF unit 41M-N has droplets 41MN$p$ each having xyz coordinates (xi, yi, zi). That way, any defective ODF units at any particular matrix location can be reprinted and corrected. It is noted that each unit in matrix 400B described above includes cannabinoid medication 300. In different embodiments, each unit 411-1 . . . 41M-N, also includes peppermint oil and other flavonoids.

From the forgoing disclosure, FIG. 1 to FIG. 4A-FIG. 4B of the present invention achieves the following objectives:

a cannabinoid medication that can maintain the CBD, THC, CBN, and terpenes ratio and/or percentage of weight in order to deliver a suitable dosage to different patients without any unwanted effects.

a cannabinoid medication that can maintain freshness of the CBD, THC, CBN, and terpenes and their relative ratio and/or percentage of weight in order to achieve the entourage effect.

Cannabinoid compounds that are characterized by oxidation resistance and heat resistance so as to prevent THC from converting into CBN.

Yet another object of the present invention is to provide a cannabinoid medication that can be delivered sublingually and easy to be absorbed by the patient's body without any side effects and degradations of the medication Few steps and more cost-effective manufacturing process than the prior art casting production to manufacture ODF products.

System and process of manufacturing ODF products that can correct defects without discarding defective units, thus improving efficiency.

System and process of manufacturing ODF products that can control the quantity, the dimension, and the geographical shapes of the ODF products.

System and process of manufacturing ODF products that can use advanced printing technology such as 4D printing.

Experiments

A. Formation of New Cannabinoid Compound 203 from THC & Unsaturated Fatty Acids

Stearic acids $CH_3(CH_2)_{16}COOH$ were used for the saturated fatty acids (n=18) and vacuum dried THC powder was used. Stearic acid is liquefied at 70° C.-100° C. into a liquid. THC powder was added into the stearic acid and stirred using a heating magnetic stirrer ARE by Velp Scientifica. The mixture is dried to remove water ($H_2O$) therefrom.

B. Reactions of CBD, CBN, Terpenes, and Unsaturated Fatty Acids

The same experiment described above was performed for CBD, CBN, and terpenes.

II. Bioavailabilities of Cannabinoid Compounds 203 ($C_{41}H_{65}O_2$) and 213 ($C_{61}H_{106}O_2$) Mixed with Coating Layer Such as HPMC, PGPR, Pullulan, and/or Gelatin Since the bioactivities of THC, CBD, CBN, terpenes have been studied and well-known, they can be used to treat cancer, epilepsy, post-traumatic stress disorder, diabetes, Crohn's disease, gout, pain relief, glaucoma, opioid dependence, alcohol abuse, insomnia, psoriasis, shingles, anorexia, asthma, fibromyalgia, rheumatoid arthritis, migraine headaches, Dravet syndrome, multiple sclerosis, autism, and menstrual pain. Cannabinoid Compounds 203 ($C_{41}H_{65}O_2$) and 213 ($C_{61}H_{106}O_2$) contain THC and CBN and long-chain fatty acids $(CH_2)_nCH_3COOH$. The saturated fatty acids (such as alearic acid) can are broke down by the human digestive enzymes and effective THC, CBD, and CBN at predetermined dosages are delivered.

III. Bioadhesiveness of Cannabinoid Compounds 203 ($C_{41}H_{65}O_2$) and 213 ($C_{61}H_{106}O_2$), and HPMC, PGPR, or Gelatin Cellulose as Coating Devices Hydroxypropylcellulose (HPC), which possesses bioadhesive properties, was used as the matrix-forming polymer. Low molecular weight polyethylene oxide and polyethylene glycol-400 were used to facilitate film processing. Butylated hydroxytoluene (BHT) was included in the formulation to further reduce oxidative degradation of the polymer and the cannabinoid compounds 203 ($C_{41}H_{65}O_2$) and 213 ($C_{61}H_{106}O_2$). A bioadhesive polymer, was also incorporated into the formulation. The polymeric systems were prepared by melting and homogenizing the polymers with other excipients followed by controlled cooling. The maximum temperatures used for the preparation of the matrices ranged from 100° C.-200° C. and the total time for preparation of each matrix varied from 75-90 min. The prepared matrices were sealed up and frozen at −18° C. These films were cut into strips for the bioadhesive studies and were also analyzed for post-production content of the cannabinoid compounds.

To investigate the thermal stability of cannabinoid compounds 203 ($C_{41}H_{65}O_2$) and 213 ($C_{61}H_{106}O_2$), a similar hot-melt cast molding method was utilized to incorporate cannabinoid compounds into the HPC matrix systems to investigate the effect of processing temperature on the stability of cannabinoid compounds and their extent of degradation within the matrix systems. For this purpose, cannabinoid compounds 203 ($C_{41}H_{65}O_2$) and 213 ($C_{61}H_{106}O_2$) were incorporated into the matrices at a 4%-10% concentration. The final temperature in the matrix preparation technique was varied to compare the post-production stability of cannabinoid compounds and the resulting other element content in the matrices. The three different processing temperatures used were 120° C., 160° C., and 200° C.

Bioadhesive measurements including peak adhesive force (PAF), area under the curve (AUC), and elongation at adhesive failure (EAF) were recorded utilizing a texture analyzer. A human intestinal mucosa was used as the model biological membrane for conducting the bioadhesion tests.

This whole system was placed at the base of the texture analyzer. Bioadhesive parameters such as work of adhesion and peak adhesive force were used to evaluate the bioadhesive strength of the polymeric matrices.

Conclusions

Cannabinoid compounds 203 ($C_{41}H_{65}O_2$) and 213 ($C_{61}H_{106}O_2$) were found to be stable under the hot-melt casting conditions. Processing temperatures up to 200° C. were utilized without imparting considerable degradation of the drug. In the matrix formulation, Cannabinoid compounds 203 ($C_{41}H_{65}O_2$) and 213 ($C_{61}H_{106}O_2$) were stable at room temperature and up to 60° C. In addition, the incorporation of 203 ($C_{41}H_{65}O_2$) and 213 ($C_{61}H_{106}O_2$) polymeric matrices led to an increase in bioadhesive strength and work of adhesion of the systems, demonstrating a very unique, significant feature of 203 ($C_{41}H_{65}O_2$) and 213 ($C_{61}H_{106}O_2$) themselves possess mucoadhesive properties. These studies have demonstrated the potential use of thermally processed intra-oral matrix systems for systemic controlled delivery of THC, CBD, CBN, and related.

Further studies and tests need to perform in order to ascertain the properties of 203 ($C_{41}H_{65}O_2$) and 213 ($C_{61}H_{106}O_2$) and their bio adhesiveness in the cellulose matrix systems.

The term "cannabis oil" as used herein refers to the isolated extract from cannabis plants. Cannabis oil is obtained from plants of the *Cannabis safiva C. indica* and *C. ruderalis* by various isolation processes, including steam distillation, organic solvent extraction, microwave-assisted organic solvent extraction, supercritical fluid extraction and cryo-mechanical methods, which are suitable for use in this invention. Crude cannabis oil, extract or concentrate so obtained can be used without any purification to produce HHC-enriched cannabis oil by hydrogenation of the oil directly to reduce the carbon-carbon double bonds of the tetrahydrocannabinoid compounds in the oil such as Δ-9-tetrahydrocannabinoic acid (THCA) and Δ-9-cannabidiolic acid (CBDA)

The flow diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A cannabinoid composition comprising: a first compound, consisting of a cannabidiol element (CBD) combined with a first fatty acid chain; and
a second compound, consisting of a $\Delta^9$ tetrahydrocannabidiol (THC) element combined with a second fatty acid chain;
wherein said first compound has a formula:

and wherein said second compound has wherein R is a long-chain hydrocarbon having the formula of $CH_3(CH_2)_n$ where n is a non-zero even integer number.

2. The cannabinoid composition of claim 1 wherein said first fatty acid and said second fatty acid are said R consisted of said single carbon bond with the formula of $CH_3(CH_2)_n$ and n equals to 18.

3. The cannabinoid composition of claim 1 further comprising a cannabis terpenoid.

4. The cannabinoid composition of claim 3 wherein said cannabis terpenoid is limonene.

5. The cannabinoid composition of claim 1 further comprising a water-soluble excipient, wherein said water-soluble excipient is configured to provide a coating to said cannabinoid compound.

6. The cannabinoid composition of claim 5 wherein said soluble excipient further comprises a gelatin.

* * * * *